United States Patent
Abner et al.

(10) Patent No.: US 11,020,098 B2
(45) Date of Patent: Jun. 1, 2021

(54) METHODS, SYSTEMS AND DEVICES FOR CRYOGENIC BIOPSY

(71) Applicant: Boston Scientific Scimed, Inc., Maple Grove, MN (US)

(72) Inventors: William Abner, Marlborough, MA (US); Allison Mary Day, Holden, MA (US); Briana Moretti, Smithfield, RI (US); John Allen Hingston, Framingham, MA (US); Amy Levasseur, Holliston, MA (US); Donald C. von Linden, Jr., Lancaster, MA (US); Sujit Tatke, Natick, MA (US); Paul Smith, Smithfield, RI (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 532 days.

(21) Appl. No.: 14/848,553

(22) Filed: Sep. 9, 2015

(65) Prior Publication Data
US 2016/0066896 A1 Mar. 10, 2016

Related U.S. Application Data

(60) Provisional application No. 62/047,809, filed on Sep. 9, 2014.

(51) Int. Cl.
| | |
|---|---|
| *A61B 10/02* | (2006.01) |
| *A61B 10/06* | (2006.01) |
| *A61B 10/04* | (2006.01) |
| *A61B 18/02* | (2006.01) |
| *A61B 18/00* | (2006.01) |

(52) U.S. Cl.
CPC ...... *A61B 10/0266* (2013.01); *A61B 10/0233* (2013.01); *A61B 10/04* (2013.01); *A61B 10/06* (2013.01); *A61B 2010/0208* (2013.01); *A61B 2018/00041* (2013.01); *A61B 2018/0262* (2013.01); *A61B 2018/0293* (2013.01)

(58) Field of Classification Search
None
See application file for complete search history.

(56) References Cited

U.S. PATENT DOCUMENTS 3,794,039 A * 2/1974 Kollner .............. A61B 18/0218
606/22
5,833,685 A * 11/1998 Tortal .................... A61B 18/02
606/23

(Continued)

OTHER PUBLICATIONS

Ferdi Akca et al., "Safety and feasibility of single-catheter ablation using remote magnetic navigation for treatment of slow-fast atrioventricular nodal reentrant tachycardia compared to conventional ablation strategies", 2013, vol. 68, No. 6, Acta Cardiologica, pp. 559-567.

(Continued)

*Primary Examiner* — Patrick Fernandes
*Assistant Examiner* — Benjamin S Melhus
(74) *Attorney, Agent, or Firm* — Bookoff McAndrews, PLLC

(57) ABSTRACT

Cryogenic biopsy assemblies are described herein that comprise a tissue acquisition device and cryogenic probe. Also disclosed are systems containing such cryogenic biopsy assemblies and methods cryogenic biopsy that employ such cryogenic biopsy assemblies.

19 Claims, 5 Drawing Sheets

(56) References Cited

U.S. PATENT DOCUMENTS

| | | | | |
|---|---|---|---|---|
| 6,039,730 | A * | 3/2000 | Rabin | A61B 18/02 606/21 |
| 6,306,132 | B1 * | 10/2001 | Moorman | A61B 10/0233 600/562 |
| 7,938,822 | B1 * | 5/2011 | Berzak | A61B 18/02 606/20 |
| 8,409,185 | B2 * | 4/2013 | Burger | A61B 18/0218 606/24 |
| 9,044,212 | B2 * | 6/2015 | LePivert | A61M 25/0045 |
| 2002/0045842 | A1 * | 4/2002 | Van Bladel | A61B 10/0266 600/584 |
| 2003/0060815 | A1 * | 3/2003 | Lalonde | A61B 18/02 606/23 |
| 2003/0195436 | A1 * | 10/2003 | Van Bladel | A61B 10/0266 600/584 |
| 2005/0182394 | A1 * | 8/2005 | Spero | A61B 10/0266 606/21 |
| 2006/0074343 | A1 * | 4/2006 | Hibner | A61B 10/0275 600/566 |
| 2007/0032723 | A1 * | 2/2007 | Glossop | A61B 1/018 600/424 |
| 2007/0055173 | A1 * | 3/2007 | DeLonzor | A61B 10/0266 600/564 |
| 2007/0191732 | A1 * | 8/2007 | Voegele | A61B 10/0266 600/564 |
| 2008/0200910 | A1 * | 8/2008 | Burger | A61B 18/02 606/20 |
| 2009/0036823 | A1 * | 2/2009 | LePivert | A61B 18/02 604/21 |
| 2010/0198206 | A1 * | 8/2010 | Levin | A61B 18/02 606/21 |
| 2010/0312141 | A1 * | 12/2010 | Keast et al. | A61B 1/00165 600/567 |
| 2011/0071427 | A1 * | 3/2011 | Fischer | A61B 10/02 600/565 |
| 2012/0059364 | A1 * | 3/2012 | Baust | A61B 18/02 606/24 |
| 2012/0065542 | A1 * | 3/2012 | Hibner et al. | A61B 10/0275 600/567 |
| 2013/0165815 | A1 * | 6/2013 | Zinn et al. | A61B 10/0275 600/567 |
| 2013/0253491 | A1 * | 9/2013 | Burr | A61B 18/0218 606/21 |
| 2014/0275767 | A1 * | 9/2014 | Baust | A61B 18/02 600/104 |
| 2014/0276037 | A1 * | 9/2014 | Johnson | A61B 10/0266 600/431 |
| 2014/0276708 | A1 * | 9/2014 | Karnik | A61B 18/02 606/21 |
| 2014/0350536 | A1 * | 11/2014 | Allison | A61F 7/00 606/21 |
| 2015/0066005 | A1 * | 3/2015 | Fan | A61B 18/0218 606/21 |
| 2016/0206295 | A1 * | 7/2016 | Kramer | A61B 18/02 |
| 2016/0354066 | A1 * | 12/2016 | Asaoka | A61B 10/02 |

OTHER PUBLICATIONS

Vikram K. Reddy et al., "Clyomap failure", Journal of Interventional Cardiac Electrophysiology, 2007, vol. 19, Issue 2, pp. 139-141.

Shinji Osada et al., "A Novel Strategy by Cryoablation for Advanced Hepatoma", Anticancer Research, 2009, vol. 29, pp. 5203-5209.

Fabrizio Drago et al., "'Time to effect' during cryomapping: a parameter related to the long-term success of accessory pathways cryoablation in children", European Society of Cardiology, Europace, 2009, vol. 11, pp. 630-634.

* cited by examiner

METHODS, SYSTEMS AND DEVICES FOR CRYOGENIC BIOPSY

CROSS-REFERENCE TO RELATED APPLICATIONS

This application claims the benefit of U.S. Provisional Application No. 62/047,809, entitled "METHODS, SYSTEMS AND DEVICES FOR CRYOGENIC BIOPSY" and filed Sep. 9, 2014, the disclosure of which is hereby incorporated by reference.

BACKGROUND

Biopsy may be defined the removal and analysis of body tissue for medical diagnosis. Typically, physicians obtain biopsy samples in order to detect abnormalities such as cancer and determine the extent to which abnormal tissue has spread. Physicians may use various biopsy instruments to acquire tissue samples from different areas of the body. During a biopsy tissue sampling procedure, a physician may use an endoscope to provide a passageway for entry of the biopsy instrument into the body.

The present disclosure relates to methods, systems and devices for biopsy, and more particularly to methods, systems and devices for cryogenic biopsy.

SUMMARY

In various aspects, the disclosure provides a cryogenic biopsy assembly that comprises (a) a tissue acquisition device and (b) a cryogenic probe comprising an elongate body having a proximal end and a distal end and a cooling tip positioned proximate to the distal end of the elongated body and configured for application of cryogenic temperatures. The tissue acquisition device may comprise, for example, a biopsy needle, forceps, or any other suitable means for capturing tissue. The biopsy needle may be between 19 gauge (1.07 mm outer diameter (o.d.)) and 25 gauge (0.51 mm o.d.) in diameter.

The tissue acquisition device may comprise a biopsy needle that comprises a distal tip and a needle lumen extending at least partially longitudinally through the biopsy needle, the needle lumen having a proximal end and a distal end terminating at the distal tip. The cooling tip of the cryogenic probe may be dimensioned to be positioned within the needle lumen. The cooling tip may be, for example, extendable from the needle lumen beyond the distal tip, extendable to a stop that is positioned within the needle lumen and proximal to the distal tip, or provided at a fixed position within the needle lumen proximal to the distal tip, among other possibilities. The cooling tip of the cryogenic probe may be configured to be inserted into the proximal end of the needle lumen, advanced through the needle lumen, and extend beyond the distal tip of the biopsy needle.

In certain embodiments, which may be used in combination with any of the above aspects and embodiments, the cryogenic biopsy assembly may include an activation mechanism for switching the assembly between a first configuration wherein the cooling tip extends beyond the distal tip of the biopsy needle and a second configuration wherein the cooling tip is retracted within the needle lumen to a position proximate the distal tip of the biopsy needle, and vice versa.

In certain embodiments, which may be used in combination with any of the above aspects and embodiments, the cryogenic biopsy assembly may include a locking mechanism for locking the cryogenic probe within the biopsy needle such that longitudinal movement between the cryogenic probe and the biopsy needle is prevented.

In certain embodiments, which may be used in combination with any of the above aspects and embodiments, the cooling tip may comprise an electrical heating element operable to heat the cooling tip, or the cooling tip may be operable to be heated by flowing pressurized gas into the cooling tip.

In certain embodiments, which may be used in combination with any of the above aspects and embodiments, the elongate body of the cryogenic probe may comprise a supply lumen configured to supply refrigerant from the proximal end of the elongate body to the cooling tip and a return lumen configured to return the refrigerant from the cooling tip to the proximal end.

In certain embodiments, which may be used in combination with any of the above aspects and embodiments, the cryogenic probe may include a hypotube having a hypotube lumen with a proximal end and a distal end, wherein the proximal end is in fluid connection with a refrigerant supply lumen. A cross-sectional area of the hypotube lumen at the distal end may be less than a cross-sectional area of the hypotube lumen at the proximal end.

In certain embodiments, which may be used in combination with any of the above aspects and embodiments, the cryogenic probe may include a hypotube having an input lumen and a plurality of exit lumens, wherein the input lumen is in fluid connection with a refrigerant supply lumen.

In various aspects, the disclosure provides a cryogenic biopsy system comprising (a) cryogenic biopsy assembly in accordance with any of the above aspects and embodiments; (b) a supply of refrigerant; and (c) a control unit operable to control temperatures of the cryogenic probe by regulating the supply of refrigerant. The cryogenic biopsy assembly may comprise a temperature sensor, wherein refrigerant flow is decreased when the temperature sensor has cooled beyond a predetermined threshold or wherein refrigerant flow is increased when the temperature sensor becomes heated beyond a predetermined threshold, or both.

In various additional aspects, the disclosure provides a method of obtaining a tissue sample from a subject comprising (a) positioning a cryogenic biopsy assembly, such as is described in the above aspects and embodiments, in a subject such that the cooling tip of the cryogenic probe extends from the distal tip of the biopsy needle into tissue of the subject, (b) cooling the cooling tip to a cryogenic temperature such that the cooling tip adheres to the tissue, (c) moving the biopsy needle relative to the cooling tip such that the cooling tip and a sample of the tissue are positioned in the needle lumen, and (d) withdrawing the cryogenic biopsy assembly and sample from the subject.

The cryogenic temperature may be above the temperature at which cell death occurs in the tissue.

In certain embodiments, which may be used in combination with any of the above aspects and embodiments, the method may further comprise reinserting the cooling tip into the subject and cryoablating tissue within the subject using the cooling tip.

In certain embodiments, which may be used in combination with any of the above aspects and embodiments, the method may further comprise warming the cooling tip thereby releasing the sample from the cooling tip.

In various additional aspects, the disclosure provides a method of obtaining a tissue sample from a subject using a cryogenic biopsy assembly, such as is described in the above aspects and embodiments, wherein the cooling tip of the cryogenic probe is fixed within the needle lumen proximate the distal tip of the biopsy needle such that a sample collection space is created in the needle lumen between the cooling tip of the cryogenic probe and the distal tip of the biopsy needle. The method comprises inserting the cryogenic biopsy assembly into tissue of the subject, cooling the cooling tip of the cryogenic probe such that the distal tip of the needle is cooled to a cryogenic temperature, capturing a sample of the tissue in the sample collection space (e.g., by advancing the assembly into tissue to be sampled, either before or after cooling), and withdrawing the cryogenic biopsy assembly and sample from the subject.

The assemblies, systems and methods described herein have various advantages relative to other technologies. For example, as discussed in more detail below, because the tissue is cooled, it can be more easily captured, allowing for the retrieval of more representative, structurally complete samples than are provided by similar methods without sample cooling. Moreover, because the tissue sample can be made to adhere to the cryogenic probe, it is readily captured. In addition, once a sample is obtained, the cryogenic probe can be used to keep the sample cold, preserving the sample until removal. Furthermore, in embodiments where the cryogenic probe can be heated, the sample may be more readily removed without damage to cell structure.

The above and other aspects, embodiments and advantages of the present disclosure will become apparent to those of ordinary skill in the art upon review of the detailed description set forth below.

DETAILED DESCRIPTION

Described herein are cryogenic biopsy assemblies and methods and systems pertaining to the same.

In various aspects, the disclosure provides a cryogenic biopsy assembly that comprises (a) a tissue acquisition device and (b) a cryogenic probe comprising an elongate body having a proximal end and a distal end and a cooling tip positioned proximate to the distal end of the elongated body and configured for application of cryogenic temperatures. The tissue acquisition device may comprise, for example, a biopsy needle (which may, for example, be hollow, bifurcated, have a sharp tip, or possess a combination of these features, among others), forceps, or any other suitable means for capturing tissue.

In various embodiments, the cryogenic biopsy assembly includes a biopsy needle and an internal cryogenic probe having a cooling tip that is configured to be cooled to cryogenic temperatures, which are defined herein as temperatures less than 0° C. Various beneficial ranges are described below. In certain embodiments, cryogenic probe extends from a distal end of the biopsy needle to cool tissue, and the biopsy needle is then advanced relative to the cryogenic probe (e.g., by advancing the needle over the cryogenic probe, by pulling the cryogenic probe back into the needle, or by a combination of the two), severing tissue and capturing a biopsy sample within the biopsy needle. After analysis of the biopsy sample, cryogenic ablation may be performed using the cryogenic probe if desired.

Figure 1:
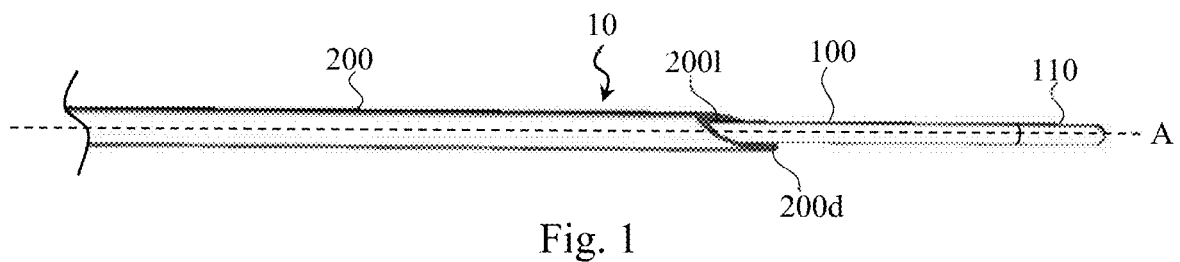
FIG. 1 is a schematic illustration of a distal end of a cryogenic biopsy assembly, according to one embodiment.

FIG. 1 illustrates a distal end of one cryogenic biopsy assembly 10 in accordance with the present disclosure, and shows the internal cryogenic probe 100 and biopsy needle 200 of the cryogenic biopsy assembly 10. The biopsy needle 200 has a sharpened distal tip 200*d* and a lumen 200*l* that extends longitudinally through at least the distal portion of the biopsy needle 200. The elongated cryogenic probe 100 has a cooling tip 110. The cryogenic probe 100 is configured to occupy the lumen 200*l* of the biopsy needle 200 and to move relative the biopsy needle 200 along a longitudinal axis A that may be common to the cryogenic probe 100 and biopsy needle 200. In the configuration shown, the cryogenic probe 100 extends beyond the distal tip 200*d* of the biopsy needle 200. Typical dimensions for the biopsy needle 200 range from 14 gauge (2.108 mm o.d.) to 25 gauge (0.5144 mm o.d.), for example, ranging from 14 to 15 to 16 to 17 to 18 to 19 to 20 to 21 to 22 to 23 to 24 to 25 gauge (i.e., ranging between any two of the preceding numerical values), more preferably, from 19 to 25 gauge. Typical dimensions for the cryogenic probe 100 range from 15 gauge to 28 gauge, for example, ranging from 15 to 16 to 17 to 18 to 19 to 20 to 21 to 22 to 23 to 24 to 25 to 26 to 27 to 28 gauge (i.e., ranging between any two of the preceding numerical values), more preferably 21 to 28 gauge, with the selected diameter allowing for sufficient clearance with respect to the inside diameter of the biopsy needle 200 to allow relative movement. Typical differences between the outer diameter of the cryogenic probe and the inside diameter of the biopsy needle range from 0.005 to 0.025 inches (0.127 to 0.635 mm) to provide sufficient clearance.

The cryogenic biopsy assembly 10 is useful, for instance, in severing and capturing a tissue sample from a subject (e.g., a human, pet, livestock, etc.) for biopsy. For example, with reference to FIG. 2A, the cooling tip 110 of the cryogenic probe 100 may first be inserted into tissue of interest and refrigerant introduced into the cryogenic probe 100, cooling the cooling tip 110 and forming a region of cooled tissue 300 around the cooling tip 110. The cooling process causes the tissue 300 to become more rigid and to adhere to the cooling tip 110. In certain embodiments, the tissue 300 is not cooled to the point of cell death. After cooling is performed, a biopsy sample is isolated as shown in FIG. 2B, whereby the biopsy needle 200 is advanced relative to the cryogenic probe 100, severing a biopsy sample 300*s* from the remainder of the cooled tissue 300. Because the cooled tissue 300 adheres to the tip 110 of the cryogenic probe 100, the cooled tissue 300 is held in place as the biopsy needle 200 is advanced relative to the cryogenic probe 100. Once the tissue sample 300s is captured within the needle 200, it can be removed from the patent in the form of a tissue core as shown in FIG. 2C. Upon removal from the assembly 10, the tissue sample can be analyzed. In certain embodiments, the cooling tip is warmed before removing the tissue sample, releasing the tissue sample from the cooling tip and minimizing damage to the tissue sample. The cooling tip may be warmed, for example, by including a heating element such as an electrical (e.g., electrically resistive) heating element in the cooling tip. Alternatively, the cryogenic probe may be rapidly pressurized to warm the cooling tip, among other options. Depending on the biopsy result, the assembly (or just the cryogenic probe portion thereof) can be used to perform tissue cryoablation as is known in the art. In this way, the assembly can be used to kill cell tissue if desired, for example, in the treatment of tumors or cancer. As a specific example, if histological results indicate cancer, the cooling portion of the assembly can be advanced along the needle pathway into the tumor and the tumor cryogenically cooled to the point of cell death (i.e., cryoablated). The cooling process may be monitored by ultrasound to ensure adequate margin.

Thus, the cryogenic probe may be initially be operated at a temperature (e.g., a temperature selected by the health care professional performing the procedure, or a temperature established through a timed cooling cycle or a computer program) whereby cell death is prevented from occurring. In addition, the cryogenic probe may be operated at a temperature (e.g., a temperature selected by the health care professional performing the procedure, or a temperature established through a timed cooling cycle or a computer program) whereby cell death is assured.

In this regard, it is well established that tissue can be frozen without causing cell death. For example, in "cryomapping" procedures known for use in cardiac ablation, the most suitable site for the ablation is determined through a transient, reversible loss of electrical function in an area of interest frozen to around −30° C. Irreversible cryoablation has been reported to occur at significantly lower temperatures (i.e., approximately −75° C.). See, e.g., V. K. Reddy et al., *J. Interv. Card. Electrophysiol.* 2007 August; 19(2): 139-141; Akca et al., *Acta Cardiol.* 2013 December; 68(6): 559-67; and F. Drago et al., *Europace.* 2009 May; 11(5): 630-4. Within the liver, cells have been reported to have different sensitivities to death by freezing, with the critical temperature for cell destruction reported as ranging from −5° C. to −50° C. See, e.g., S. Osada et al., *Anticancer Research* 29: 5203-5210 (2009). In the methods described herein, tissue need only be cooled until sufficient hardness is obtained to improve sampling and biopsy results. Thereafter, the tissue can be cooled as required to kill tumor tissue with sufficient margin.

In certain specific embodiments, the cryogenic probe is cooled sufficiently to achieve a targeted tissue temperature of about 0 to −30° C. during tissue sampling, preferably about −5° C. to −15° C., more preferably about −10° C., among other possible values. In certain embodiments, the temperature of the cryogenic probe may be controlled such that the probe temperature will not go lower than −35 C.° during tissue sampling, among other values. In certain specific embodiments, the cryogenic probe is cooled sufficiently to achieve a targeted minimum tissue temperature of less than about −60° C. during cryoablation, preferably about −70° C. to −80° C., more preferably about −75° C.

The methods and devices of the present disclosure may be indicated for use in biopsy and ablation of a wide variety of malignant or benign tissue, including liver tissue, pancreatic tissue, biliary tissue and urologic tissue, among others. In specific embodiments, the methods and devices are indicated for the endoscopic biopsy and ablation of malignant or benign tissue in the liver or pancreas of subjects with locally advanced metastic disease who are not suitable candidates for curative surgical resection.

The devices, systems and methods described have various benefits relative to other technologies. For example, because the tissue is cooled, it can be more easily cored by the needle, rather than being deformed by the needle, allowing for the retrieval of more representative, structurally complete samples than are provided by similar methods without sample cooling. Consequently, less deployments may be required to obtain sufficient tissue, providing a more representative sample of the region. Moreover, because the sample can be made to adhere to the cryogenic probe, it is readily captured by the biopsy needle in tandem with the cutting action of the needle. In addition, because tissue deformation is minimized, less collateral damage is done to surrounding tissue. Furthermore, once the sample is obtained, the cryogenic probe can be used to keep the sample cold, preserving the sample until removal from the biopsy assembly. In order to release the sample, the probe can be heated, for example, using a heating element or rapidly pressurizing the probe to warm the cooling tip, which allows the sample to be removed cleanly without damage to cell structure.

Figure 2A:
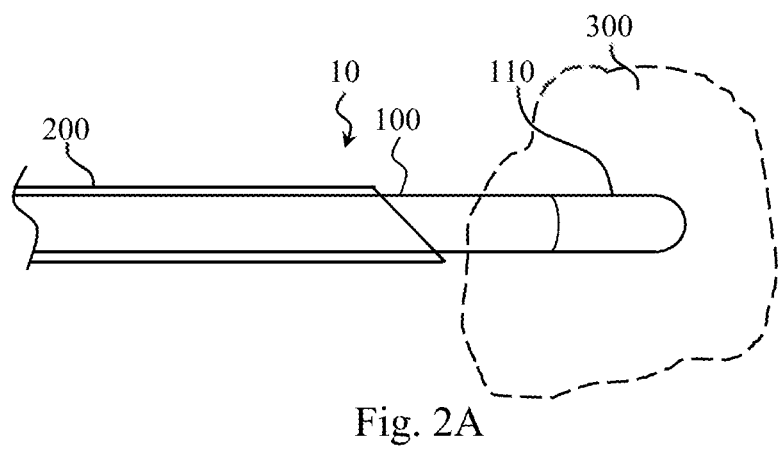
FIG. 2A, FIG. 2B and FIG. 2C are schematic illustrations of a method of using a cryogenic biopsy assembly like that of FIG. 1, according to one embodiment.
Figure 2B:
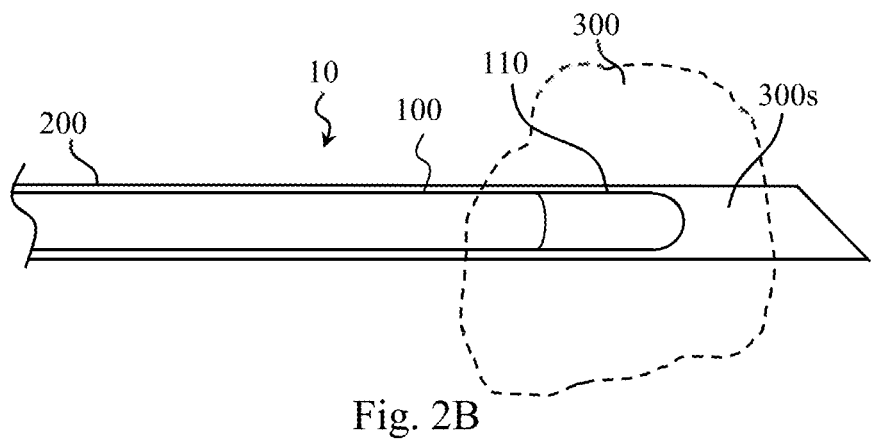
Figure 2C:
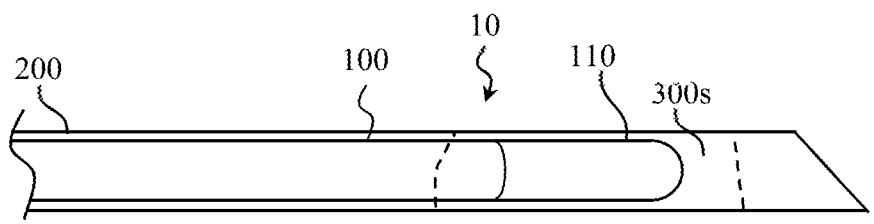
Figure 7:
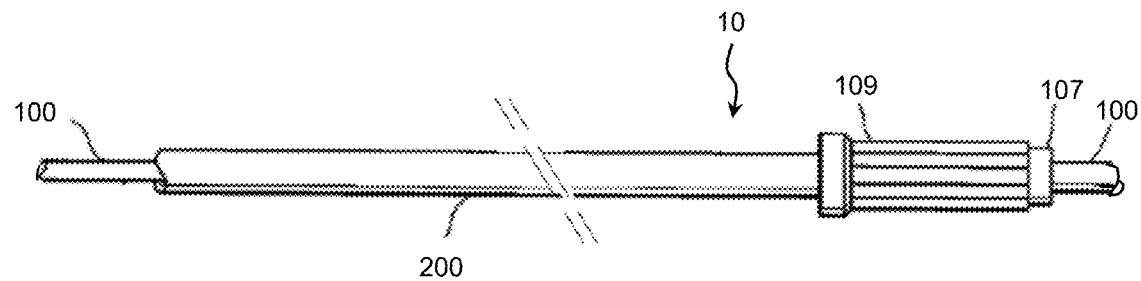
FIG. 7 is a schematic illustration of an operating mechanism for use in conjunction with the cryogenic biopsy assembly.

As noted in conjunction with FIGS. 2A-2C, during a biopsy sampling procedure in accordance with the present disclosure, a biopsy sample is taken by advancing the biopsy needle 200 relative to the cryogenic probe 100 within the cryogenic biopsy assembly 10. One simple activation mechanism for performing this function is illustrated in FIG. 7, which shows a finger-grip section 109 at a proximal end of the biopsy needle 200, which is configured to facilitate the ability of a healthcare provider to grip the biopsy needle 200. A releasable locking mechanism 107 configured to releasably lock the biopsy needle 200 to the cryogenic probe 100 may be mounted at a proximal end of the finger-grip section 109. Although illustrated as a simplified structure for clarity and ease of illustration, more elaborate structures could be provided on the proximal end of the cryogenic biopsy assembly 10, which have an activation mechanism which can be activated to move the biopsy needle 200 relative to the cryogenic probe 100 therein, and which can have a locking mechanism to releasably secure the biopsy needle 200 to the cryogenic probe 100. Such activation mechanisms are generally known in the medical arts and may include, for example, a thumb wheel, trigger, lever coaxial slide or other activation mechanism suitable for advancing and/or retracting a hollow cylindrical member relative to another member disposed within the hollow cylindrical member. A variety of suitable locking mechanisms that may be used to clamp or otherwise releasably lock the biopsy needle 200 to the cryogenic probe 100 are conventionally known, examples of which include clamps, thumbscrews, positive stops, incremental detent positions, compression stops or other locking mechanism.

Figure 8:
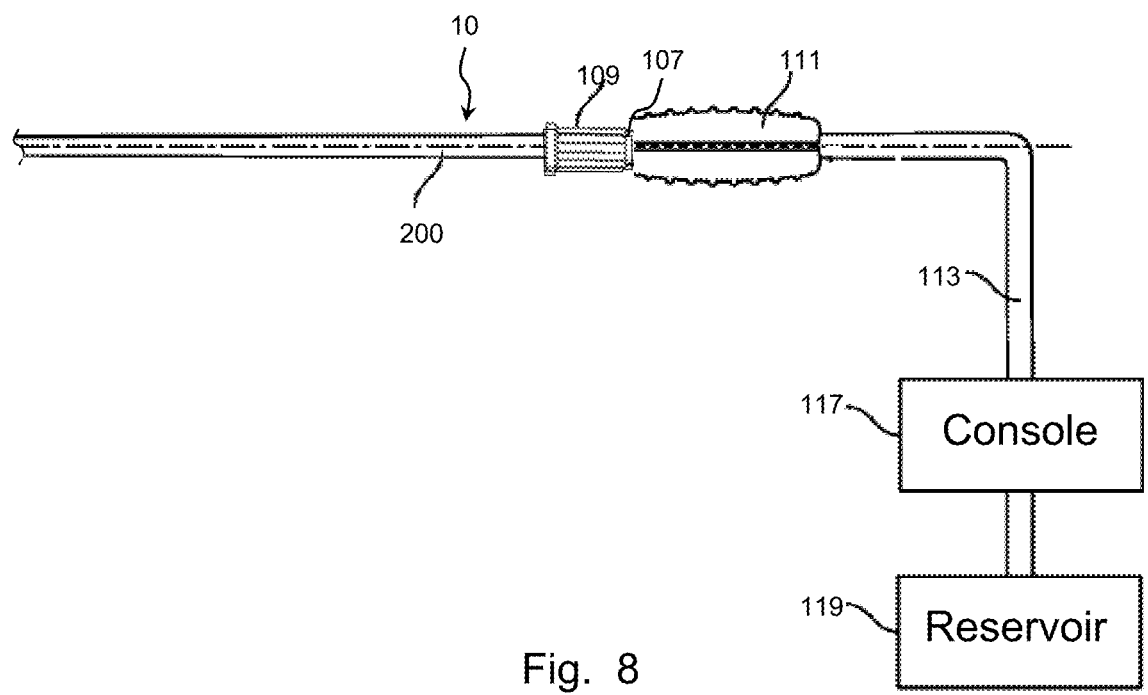
FIG. 8 is a schematic illustration of a cryogenic biopsy system, according to one embodiment.

FIG. 8 is a schematic illustration of a system for performing cryogenic biopsies. A proximal end of a cryogenic biopsy assembly 10 is shown, which includes a finger-grip section 109 like that illustrated in FIG. 7 along with a handle 111. As with the finger-grip, although a simplified structure is illustrated for clarity and ease of illustration, more elaborate structures could be provided as handles, for example, a handle comprise an ergonomic groove like that shown in FIG. 6, among many other possibilities. Cryogenic biopsy assembly 10 is coupled with a cryogenic console 117 via a supply line 113 in order to supply refrigerant from a refrigerant source such as a cryogenic reservoir 119 to the cryogenic biopsy assembly 10. The supply line 113 also optionally returns cryogenic fluid from the cryogenic biopsy assembly 10 to the refrigerant source. The flow of refrigerant to and from the cryogenic biopsy assembly 10 may be controlled from a control unit within the console 117, which regulates and controls the temperature and/or pressure of the refrigerant introduced into the cryogenic biopsy assembly 10. The console 117 may provide for appropriate discharge or recycle of any returned refrigerant. The console 117 is also optionally capable of pressurizing the cryogenic biopsy assembly 10, or supplying electrical current to the cryogenic biopsy assembly 10, for active warming. Alternatively, or in addition, controls (not shown) may be associated with the cryogenic biopsy assembly 10 to regulate and control the temperature and/or pressure of the refrigerant introduced into the cryogenic probe (and thus the temperature of the cryogenic probe). The cryogenic biopsy assembly 10 may also be provided with a mechanism for determining the surface temperature of the cooling tip and provide the user and/or console with that data. To this end, the outer surface of the cooling tip may be provided with a temperature measuring device, such as a thermocouple. Signals generated by the thermocouple may be transmitted via wires or wirelessly to the cryogenic console 117, where the temperature data may be displayed and/or input into a computer algorithm controlling the temperature and/or pressure of the refrigerant introduced into the cryogenic biopsy assembly 10.

A variety of refrigerants may be employed to cool cryogenic biopsy assemblies in accordance with the present disclosure, including gaseous refrigerants, liquid refrigerants and near- and super-critical refrigerants. Common gaseous refrigerants include nitrous oxide and argon systems, which typically achieve cooling by expansion of the pressurized gases through a Joule-Thomson expansion element such as a small orifice, throttle, or other type of flow constriction. An example of a liquid refrigerant is liquid nitrogen, which is introduced into the cryogenic probe in a liquid state and, depending on the exit temperature of the refrigerant, in either a liquid or vapor state. Other refrigerants that can be used in conjunction with liquid cooling include hydrocarbons and halocarbons (including chlorocarbons, fluorocarbons and chlorofluorocarbons), several of which are listed here, along with chemical formula, normal freezing point (FP) and normal boiling point (BP) of each: R218 ($C_3F_8$) (FP −150° C., BP −36.7° C.), R124 ($C_2HClF_4$) (FP −199° C., BP −12.1° C.), R290 ($C_3H_8$) (FP −188° C., PB −42° C.), R1270 ($C_3H_6$) (FP −185° C., PB −47.7° C.), R600A (i-$C_4H_{10}$) (FP −159.5°, C PB −11.8° C.). Other refrigerants include fluids that are introduced in a near-critical or super-critical state, which fluids have gas-like viscosity and is thus readily transported through small diameter lumens and orifices.

Figure 3A:
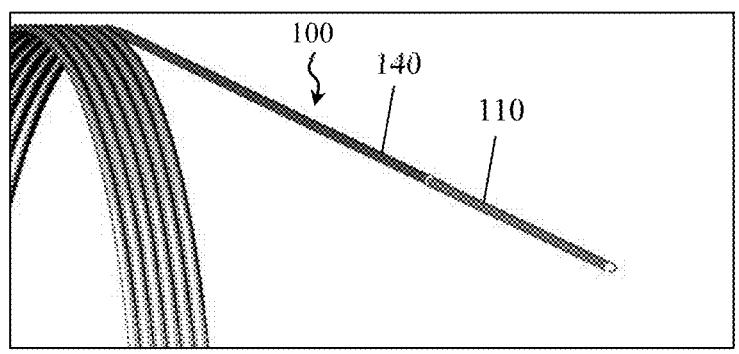
FIG. 3A is a schematic perspective view of a cryogenic probe, according to one embodiment.
Figure 3B:
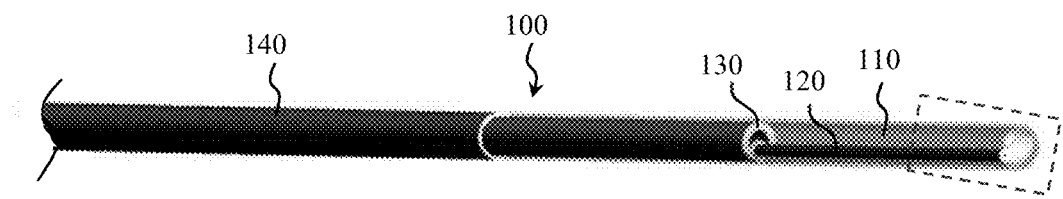
FIG. 3B is a schematic perspective view of a distal end of the cryogenic probe of FIG. 3A.
Figure 4A:
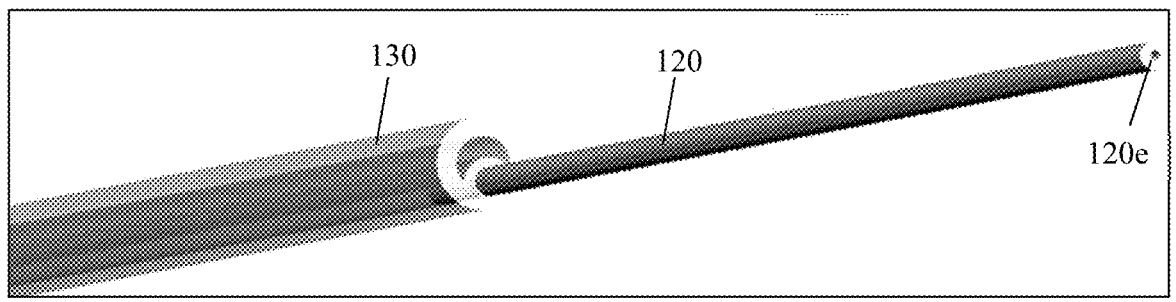
FIG. 4A is a schematic perspective view of a distal end of a hypotube and multilumen tubing of the cryogenic probe of FIGS. 3A-3B.
Figure 4B:
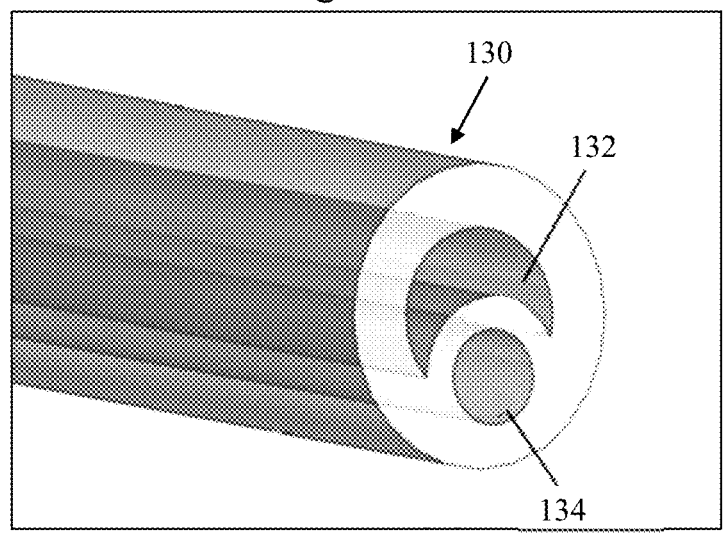
FIG. 4B is a schematic perspective view of a distal end of the multilumen tubing of FIG. 4A.

Further details of the cryogenic probe portion of the cryogenic biopsy assembly will now be described. Turning to FIGS. 3A and 3B, a distal end of a cryogenic probe 100 is illustrated and includes a flexible multilumen tube 130 for refrigerant supply and return. The multilumen tube 130 may be formed, for example, from a suitable polymer, for example, from a fluoropolymer such as polytetrafluoroethylene (PTFE), fluorinated ethylene propylene (FEP), or a terpolymer of ethylene, tetrafluoroethylene and hexafluoropropylene (EPEP), a co-extrusion of EFEP and polyether block amide (PEBA), or pure polyamide, among others. In some embodiments, an additional insulating jacket (not shown) may be provided over the multilumen tube 130. The cryogenic probe 100 further includes a cooling tip 110 in the form of a hollow tube with a rounded end. As noted above, typical dimensions for the diameter of the cryogenic probe 100 range from 15 gauge to 28 gauge. The length of the cooling tip may vary widely, typically ranging from 1 to 10 cm in length. In a specific embodiment, for example, the cooling tip may be 24 gauge in width and 2.5 cm in length, among many other possible dimensions. The cooling tip 110 may be manufactured, for example, from a suitable thermally conductive metal or metal alloy, for example, from stainless steel, aluminum, aluminum alloys, or nitinol (preferably with transition temperature below operating temperature). Aluminum and aluminum alloys may be advantageous in that they are very malleable and ductile and can be readily shapeable. Although a cooling tip 110 in the form of a hollow tube with a rounded end is shown, in other embodiments, the cooling tip may have a sharpened end for improved tissue penetration. In specific embodiments, the cooling tip 110 interfaces seamlessly with the insulating jacket 140 over a portion of the multilumen tubing 130 as shown. The cryogenic probe 100 contains a hypotube 120 having one or more refrigerant release locations. In the embodiment shown, the hypotube 120 interfaces with the supply lumen 134 of the multilumen tubing 130 as shown in FIGS. 4A and 4B. Also shown is a return lumen 132 for return of refrigerant.

Figure 5A:
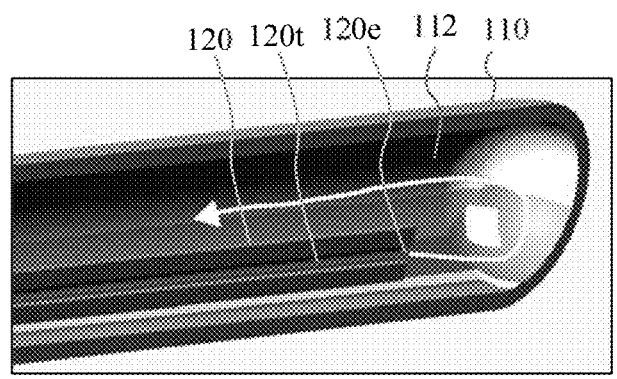
FIG. 5A is a schematic cutaway view of a distal end of the cryogenic probe of FIGS. 3A-3B.
Figure 5B:
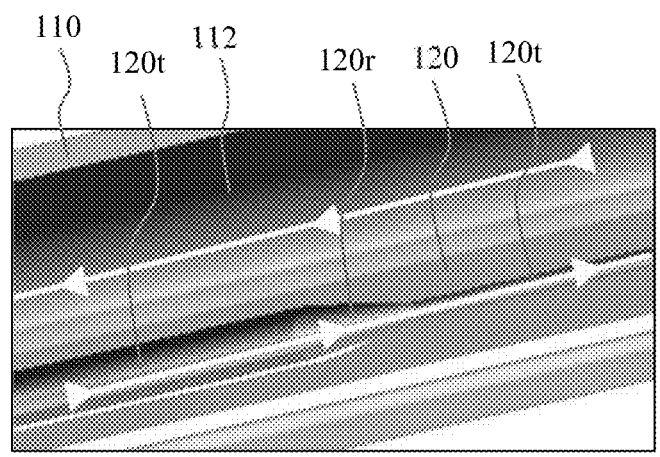
FIG. 5B is a schematic cutaway view of a portion of the cryogenic probe of FIGS. 3A-3B.

Further detail regarding the hypotube 120 can be seen in FIG. 5A and FIG. 5B. As seen from the schematic cutaway view of FIG. 5A, refrigerant passes through hypotube 120 via a lumen 120t. The hypotube may be formed from any suitable material, for example, a suitable metal or metal alloy, such as aluminum 1100 (commercially pure, 99% aluminum), 2024 aluminum alloy (an aluminum alloy, with copper as the primary alloying element), 6061 aluminum alloy (an aluminum alloy, containing magnesium and silicon as its major alloying elements) or other suitable alloy. As shown, refrigerant passing through the lumen 120t, specifically, from the proximal end of the lumen to the distal end of the lumen, passes through a region 120r where the diameter of the lumen 120t is reduced. For example, the lumen may undergo a reduction in diameter ranging from about 10% or less to 70% or more, for example, ranging from 10% to 20% to 30% to 40% to 50% to 60% to 70% (i.e., ranging between any two of the preceding numerical values), or a reduction in cross-sectional area ranging from about 20% or less to 90% or more, for example, ranging from 20% to 30% to 40% to 50% to 60% to 70% to 80% to 90% (i.e., ranging between any two of the preceding numerical values). The reduction of lumen 120t diameter within the hypotube 120 results, for example, in improved heat transfer as a result of an increase in refrigerant velocity and, in some cases, turbulence. In one particular embodiment, the lumen may be reduced from a diameter of 0.008" (0.20 mm) necking down to a diameter of about 0.004" (0.10 mm) (corresponding to a 50% reduction in diameter and a 75% reduction in cross-sectional area), among many other possibilities. The refrigerant is then expelled from a refrigerant release location in the hypotube 120, specifically an exit lumen (e.g., exit hole) 120e in the hypotube 120, and into the cooling tip where it cools the thermally conductive cooling tip to a desired temperature. The refrigerant then flows back out through the return lumen 132 (see, e.g., FIGS. 4A-4B).

Although a single refrigerant release location is provided in the end of the hypotube 120 in the embodiment shown, in other embodiments, multiple exit lumens (e.g., multiple exit holes) may be employed. For example, 2, 3, 4, 5, 6, 7, 8, 9, 10 or more exit lumens may be employed in the end of the hypotube 120, the side of the hypotube 120, or both the end and side of the hypotube 120.

Figure 6:
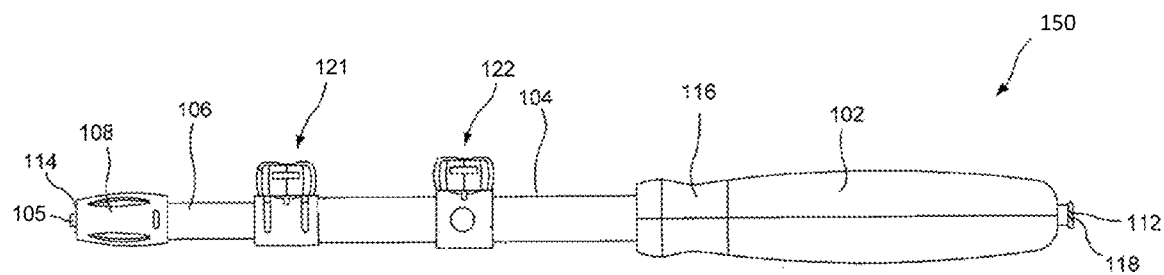
FIG. 6 is a schematic illustration of an actuation device for use in conjunction with the cryogenic biopsy assembly.

Cryogenic biopsy assemblies in accordance with the present disclosure may be used in conjunction with other devices that assist with the procedures performed by the cryogenic biopsy assemblies. Referring to FIG. 6, an actuation device 150 for use in the present disclosure may comprise an elongated body having a proximal handle portion 102, a central portion 104, a distal portion 106 and an attachment portion 108 located at a distal end thereof, the attachment portion 108 permitting attachment with an endoscope or other device for insertion into a living body in an operative configuration. The proximal handle portion 102 may comprise an ergonomic groove 116 formed adjacent a distal end thereof to aid in gripping and manipulation thereof. A lumen 105 extends through the actuation device 150 from a proximal end 112 to a distal end 114. The lumen 105 extends proximally from the proximal handle portion 102 by a predetermined distance and comprises an opening 118 opening into the lumen 105 to permit insertion of a cryogenic biopsy assembly as described herein (or other device) therethrough. The proximal handle portion 102, central portion 104 and distal portion 106 are arranged relative to one another in a telescoping arrangement. Thus, proximal refraction of the distal portion 106 causes the distal portion 106 to be withdrawn into the central portion 104, and vice versa. Similarly, proximal refraction of the central portion 104 causes the central portion 104 to be withdrawn into the handle portion 102, and vice versa. As also shown in FIG. 6, the central portion 104 further comprises a first mechanism 121 and a second mechanism 122 configured to selectively limit a proximal-distal movement of the distal portion 106 relative to the central portion 104 and movement of the central portion 104 relative to the proximal handle portion 102. Where the position of the inserted cryogenic biopsy assembly is fixed relative to the handle portion, retraction of the central portion 104 and distal portion 106 will permit a greater portion of the cryogenic biopsy assembly to be exposed at a distal end of the actuation device 150. The central portion 104, although connected to the proximal handle portion 102, may remain rotatable relative thereto, such that rotation of the proximal handle portion 102 and the lumen 105 does not result in a rotation of the central portion 104.

When inserted through the lumen 105, the cryogenic biopsy assembly may be moved proximally and distally relative to the actuation device 150 by application of a sufficient force to a proximal end of the cryogenic biopsy assembly. In certain embodiments, an inner wall of a portion of the lumen 105 extending through the proximal handle portion 102 comprises a suitable mechanism (e.g., radial abutments or a treated surface, not shown) to permit a frictional or mechanical engagement with an outer wall of a cryogenic biopsy assembly to be inserted therethrough. The cryogenic biopsy assembly may also comprise an abutment, a recess or a treated surface to permit such an engagement. In some embodiments, the cryogenic biopsy assembly may be prevented from being rotated relative to the handle portion 102 such that rotation of the cryogenic biopsy assembly can be facilitated by a rotation of the proximal handle portion 102.

In accordance with an exemplary method of the present application, an endoscope may be attached to the attachment portion 108 and guided to a target location within the body in a conventional manner (e.g., under visual observation via the endoscope). Prior to advancement of the endoscope, the central and distal portions 104, 106 of the actuation device 150 may be manipulated to a desired orientation, with the first and second mechanisms 121, 122 tightened to lock the actuation device 150 in the desired configuration. For example, the distal portion 106 may be extended to a length selected such that, when a cryogenic biopsy assembly is inserted into the lumen 105 and through the endoscope, it may be movable to a deployed position in which the distal end of the cryogenic biopsy assembly projects distally beyond a distal end of the endoscope by a desired distance. In some embodiments, the cryogenic biopsy assembly may be inserted through the actuation device 150 into the working channel of the endoscope until the proximal end of the cryogenic biopsy assembly engages with and is locked in position at a proximal end of the actuation device 150. Once the endoscope is in position, the cryogenic biopsy assembly is positioned such that a distal end of the cryogenic biopsy assembly extends distally from the endoscope by the desired distance, for example, under the guidance of an imaging device, as those skilled in the art will understand. Once the cryogenic biopsy assembly is properly positioned in the tissue, the tissue is cooled using the cooling tip of the cryogenic probe and a sample obtained using a suitable tissue acquisition device. For example, a biopsy needle may be advanced relative to the cooling tip to sever and capture a tissue sample from the remainder of the tissue as described above, at which point the cryogenic biopsy assembly and tissue sample are withdrawn from the endoscope and actuation device.

Various alternative techniques may also be employed in the treatment of a living subject. For example, in some embodiments, rather than being movable within a biopsy needle, the cryogenic probe may be fixed within a biopsy needle proximate the distal tip of the biopsy needle such that a sample collection space is created in the needle lumen between the cooling tip of the cryogenic probe and the distal tip of the biopsy needle. As another example, in some embodiments, rather than being disposed within the tissue acquisition device (e.g., biopsy needle), the cryogenic probe may be used externally and in tandem with the tissue acquisition device. In a specific embodiment, the cryogenic probe may be deployed externally to the endoscope through an accessory or attachment, or introduced by means of laparoscopic or surgical induction for the purpose described in this disclosure. In some embodiments, the cryogenic biopsy assembly may be inserted using a catheter, without the use of an endoscope.

Although various embodiments are specifically illustrated and described herein, it will be appreciated that modifications and variations of the present disclosure are covered by the above teachings and are within the purview of the appended claims without departing from the spirit and intended scope of the disclosure.

What is claimed is:

1. A cryogenic biopsy assembly comprising:
    a cryogenic probe comprising:
        a flexible multi-lumen tube having a proximal end and a distal end, wherein the flexible multi-lumen tube defines a supply lumen and a return lumen;
        a hypotube defining a hypotube lumen, wherein the hypotube lumen is in fluid communication with the supply lumen via a proximal opening of the hypotube and a distal opening of the flexible multi-lumen tube, wherein the hypotube defines a refrigerant release opening, wherein the hypotube is formed from a first material, wherein the multilumen tube is formed from a second material, and wherein the first material differs from the second material; and a cooling tip defining a cooling tip lumen and having a closed distal end, wherein a distal end of the flexible multi-lumen tube and an entirety of the hypotube are disposed within the cooling tip lumen, and wherein the cooling tip lumen is in fluid communication with the hypotube lumen via the refrigerant release opening;

wherein the supply lumen is configured to supply a refrigerant from the proximal end of the flexible multi-lumen tube to the distal end of the flexible multi-lumen tube, through the hypotube, and out of the refrigerant release opening, and wherein the return lumen is configured to return refrigerant released from the refrigerant release opening of the supply lumen to the proximal end of the flexible multi-lumen tube.

2. The cryogenic biopsy assembly of claim 1, wherein the hypotube lumen includes a proximal portion having a first diameter, and a distal portion having a second diameter, and wherein the second diameter is smaller than the first diameter.

3. The cryogenic biopsy assembly of claim 1, wherein the cryogenic probe further includes an insulating jacket disposed about an outer surface of the multi-lumen tube.

4. The cryogenic biopsy assembly of claim 3, wherein the insulating jacket interfaces seamlessly with the cooling tip.

5. The cryogenic biopsy assembly of claim 1, further comprising an actuation device, wherein the actuation device includes an attachment portion facilitating attachment of the actuation device to an endoscope.

6. The cryogenic biopsy assembly of claim 5, wherein the actuation device includes a distal portion and a proximal portion, wherein the distal portion is configured to be selectively telescopically collapsed within the proximal portion.

7. The cryogenic biopsy assembly of claim 6, wherein the distal portion is rotatable relative to the proximal portion.

8. The cryogenic biopsy assembly of claim 5, wherein the actuation device defines an actuation device lumen having a proximal opening and a distal opening, and wherein the cryogenic probe is configured to be removably inserted into the proximal opening of the actuation device lumen and advanced through the actuation device lumen such that a distal end of the cryogenic probe extends past the distal opening of the actuation device lumen.

9. The cryogenic biopsy assembly of claim 8, wherein a surface of the actuation device lumen includes a first feature configured to interact with a second feature on an outer surface of the cryogenic biopsy assembly, and where an interaction between the first feature and the second feature inhibits at least one of distal movement or rotational movement of the cryogenic biopsy assembly relative to the actuation device.

10. The cryogenic biopsy assembly of claim 1, wherein a wall separates the supply lumen from the return lumen, and wherein the wall defines an outer surface of the supply lumen and an outer surface of the return lumen.

11. The cryogenic biopsy assembly of claim 1, wherein the return lumen has a non-circular cross-sectional shape.

12. The cryogenic biopsy assembly of claim 1, wherein at least a portion of the supply lumen is radially outward of at least a portion of the return lumen.

13. The cryogenic biopsy assembly of claim 1, wherein the supply lumen and the return lumen are formed of a single, unitary structure.

14. A method of obtaining a tissue sample from a subject comprising:

attaching an actuation device to an endoscope, wherein the actuation device defines an actuation device lumen terminating at proximal and distal openings;

positioning at least a portion of a cryogenic biopsy assembly in the subject, wherein the cryogenic biopsy assembly includes a cryogenic probe including:

a flexible multi-lumen tube having a proximal end and a distal end, wherein the flexible multi-lumen tube defines a supply lumen and a return lumen, and wherein at least a portion of the supply lumen is radially outward of at least a portion of the return lumen;

a hypotube defining a hypotube lumen, wherein the hypotube lumen is in fluid communication with the supply lumen via a proximal opening of the hypotube and a distal opening of the flexible multi-lumen tube, wherein the hypotube defines a refrigerant release opening, wherein the hypotube is formed from a first material, wherein the multilumen tube is formed from a second material, and wherein the first material differs from the second material; and a cooling tip defining a cooling tip lumen and having a closed distal end, wherein the cooling tip lumen is in fluid communication with the hypotube lumen via the refrigerant release opening;

wherein the positioning step includes:

inserting a distal end of the cryogenic probe into the proximal opening of the actuation device lumen and advancing the distal end of the cryogenic probe through the actuation device lumen until the cooling tip of the body extends from the distal opening of the actuation device lumen into a working channel of the endoscope; and advancing the distal end of the cryogenic probe through the working channel until the distal end of the cryogenic probe extends beyond a distal end of the working channel;

cooling the cooling tip to a cryogenic temperature such that the cooling tip adheres to the tissue; and withdrawing the at least the portion of the cryogenic biopsy assembly from the subject.

15. The method of claim 14, wherein the actuation device includes a distal portion and a proximal portion, further comprising telescopically collapsing the distal portion within the proximal portion.

16. The method of claim 14, wherein a surface of the actuation device lumen includes a first feature configured to interact with a second feature on an outer surface of the cryogenic biopsy assembly, and where an interaction between the first feature and the second feature inhibits at least one of distal movement or rotational movement of the cryogenic biopsy assembly relative to the actuation device.

17. A cryogenic biopsy assembly comprising:

a cryogenic probe including:

a flexible multi-lumen tube having a proximal end and a distal end, wherein the flexible multi-lumen tube defines a supply lumen and a return lumen, wherein the supply lumen is configured to supply a refrigerant from the proximal end of the flexible multi-lumen tube to the distal end of the flexible multi-lumen tube, wherein the return lumen is configured to return refrigerant to the proximal end of the flexible multi-lumen tube, wherein a wall separates the supply lumen from the return lumen, and wherein the wall defines an outer surface of the supply lumen and an outer surface of the return lumen; and a cooling tip defining a cooling tip lumen and having a closed distal end, wherein the distal end of the flexible multi-lumen tube is disposed within the cooling tip lumen, and wherein the cooling tip lumen is in fluid communication with the supply lumen and the return lumen.

18. The cryogenic biopsy assembly of claim 17, wherein the cryogenic probe further includes a hypotube defining a hypotube lumen, wherein the hypotube lumen is in fluid communication with the supply lumen via a proximal opening of the hypotube and a distal opening of the flexible multi-lumen tube, wherein the hypotube defines a refrigerant release opening, and wherein the cooling tip lumen is in fluid communication with the hypotube lumen via the refrigerant release opening.

19. The cryogenic biopsy assembly of claim 18, wherein the flexible multi-lumen tube is formed from a first material that includes a polymer, wherein the hypotube is formed from a second material, and wherein the second material differs from the first material.

* * * * *